United States Patent

Ball

(10) Patent No.: US 9,420,388 B2
(45) Date of Patent: Aug. 16, 2016

(54) ELECTROMAGNETIC BONE CONDUCTION HEARING DEVICE

(71) Applicant: Vibrant Med-El Hearing Technology GmbH, Innsbruck (AT)

(72) Inventor: Geoffrey R. Ball, Axams (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 193 days.

(21) Appl. No.: 13/780,193

(22) Filed: Feb. 28, 2013

(65) Prior Publication Data

US 2014/0012069 A1 Jan. 9, 2014

(51) Int. Cl.
- *H04R 25/00* (2006.01)
- *A61N 1/375* (2006.01)
- *A61N 1/08* (2006.01)
- *A61N 1/36* (2006.01)
- *A61N 1/37* (2006.01)

(52) U.S. Cl.
CPC *H04R 25/60* (2013.01); *A61N 1/08* (2013.01); *A61N 1/36032* (2013.01); *A61N 1/375* (2013.01); *H04R 25/00* (2013.01); *A61N 1/3718* (2013.01)

(58) Field of Classification Search
CPC .. H04R 25/00; H04R 25/606; H04R 2460/13; H04R 2225/67; A61N 1/36032
USPC .................. 600/25; 381/151, 326; 607/55–57
See application file for complete search history.

(56) References Cited

U.S. PATENT DOCUMENTS

| 3,487,403 A | 12/1969 | Pihl ............................... 340/373 |
| 3,573,812 A | 4/1971 | Pihl ............................... 340/373 |

(Continued)

FOREIGN PATENT DOCUMENTS

| EP | 2031896 | 4/2009 | ............ H04R 25/00 |
| GB | 1468890 | 3/1977 | |

(Continued)

OTHER PUBLICATIONS

Bromberg & Sunstein LLP, Response A filed May 14, 2007 to Office Action dated Feb. 12, 2007, pertaining to U.S. Appl. No. 11/158,322, 14 pages.

(Continued)

*Primary Examiner* — Samuel Gilbert
(74) *Attorney, Agent, or Firm* — Sunstein Kann Murphy & Timbers LLP

(57) ABSTRACT

An external component for a bone conduction hearing implant is described. An external housing is fixedly attached on the skin of a hearing implant patient over an implanted bone conduction hearing transducer. An electromagnetic drive coil arrangement is fixed within the external housing for conducting electrical current to develop electromagnetic drive signals. An attachment magnet arrangement is suspended within the external housing by a flexible spring arrangement and magnetically coupled to the drive coil arrangement and to a corresponding implant magnet arrangement within the implanted bone conduction transducer. The electromagnetic drive signals magnetically interact with the attachment magnet arrangement which reacts by vibrating on the spring arrangement and magnetically interacting with the implant magnet arrangement to generate a bone conduction vibration signal by the implanted bone conduction hearing transducer for perception by the patient as sound.

4 Claims, 5 Drawing Sheets

(56) References Cited

U.S. PATENT DOCUMENTS

| | | | |
|---|---|---|---|
| 3,801,767 A | 4/1974 | Marks | 200/161 |
| 3,987,967 A | 10/1976 | Kuznetsov et al. | 241/1 |
| 4,038,990 A | 8/1977 | Thompson | 128/419 PG |
| 4,199,741 A | 4/1980 | Serrus Paulet | 335/206 |
| 4,257,936 A | 3/1981 | Matsumoto et al. | 524/413 |
| 4,317,969 A | 3/1982 | Riegler et al. | 200/52 R |
| 4,549,532 A | 10/1985 | Baermann | 600/15 |
| 4,596,971 A | 6/1986 | Hirabayashi et al. | 335/205 |
| 4,628,907 A | 12/1986 | Epley | 128/1.6 |
| 4,785,816 A | 11/1988 | Dow et al. | 128/660 |
| RE32,947 E | 6/1989 | Dormer et al. | 128/420.6 |
| 4,868,530 A | 9/1989 | Ahs | 335/207 |
| 4,918,745 A | 4/1990 | Hutchison | 455/41 |
| 5,015,224 A | 5/1991 | Maniglia | 600/25 |
| 5,183,056 A | 2/1993 | Dalen et al. | 128/782 |
| 5,434,549 A | 7/1995 | Hirabayashi et al. | 335/229 |
| 5,456,654 A | 10/1995 | Ball | 600/25 |
| 5,538,219 A | 7/1996 | Osterbrink | 251/129.15 |
| 5,554,096 A | 9/1996 | Ball | 600/25 |
| 5,624,376 A | 4/1997 | Ball et al. | 600/25 |
| 5,630,835 A | 5/1997 | Brownlee | 607/60 |
| 5,716,407 A | 2/1998 | Knapp et al. | 623/11 |
| 5,724,014 A | 3/1998 | Leikus et al. | 335/4 |
| 5,749,912 A | 5/1998 | Zhang et al. | 607/57 |
| 5,800,336 A | 9/1998 | Ball et al. | 600/25 |
| 5,857,958 A | 1/1999 | Ball et al. | 600/25 |
| 5,877,664 A | 3/1999 | Jackson, Jr. | 335/205 |
| 5,897,486 A | 4/1999 | Ball et al. | 600/25 |
| 5,913,815 A | 6/1999 | Ball et al. | 600/25 |
| 6,040,762 A | 3/2000 | Tompkins | 340/426 |
| 6,067,474 A | 5/2000 | Schulman et al. | 607/57 |
| 6,175,767 B1 | 1/2001 | Doyle, Sr. | 607/57 |
| 6,178,079 B1 | 1/2001 | Renger | 361/118 |
| 6,178,353 B1 | 1/2001 | Griffith et al. | 607/61 |
| 6,190,305 B1 | 2/2001 | Ball et al. | 600/25 |
| 6,208,235 B1 | 3/2001 | Trontelj | 340/10.1 |
| 6,208,882 B1 | 3/2001 | Lenarz et al. | 600/379 |
| 6,217,508 B1 | 4/2001 | Ball et al. | 600/25 |
| 6,219,580 B1 | 4/2001 | Faltys et al. | 607/57 |
| 6,292,678 B1 | 9/2001 | Hall et al. | 600/374 |
| 6,295,472 B1 | 9/2001 | Rubinstein et al. | 607/55 |
| 6,313,551 B1 | 11/2001 | Hazelton | 310/12 |
| 6,348,070 B1 | 2/2002 | Teissl et al. | 623/11.11 |
| 6,358,281 B1 | 3/2002 | Berrang et al. | 623/10 |
| 6,475,134 B1 | 11/2002 | Ball et al. | 600/25 |
| 6,505,062 B1 | 1/2003 | Ritter et al. | 600/407 |
| 6,506,987 B1 | 1/2003 | Woods | 290/61.62 |
| 6,522,909 B1 | 2/2003 | Garibaldi et al. | 600/424 |
| 6,838,963 B2 | 1/2005 | Zimmerling et al. | 335/205 |
| 7,091,806 B2 | 8/2006 | Zimmerling et al. | 335/207 |
| 7,190,247 B2 | 3/2007 | Zimmerling | 335/205 |
| 7,266,209 B1 | 9/2007 | House | 381/331 |
| 7,338,035 B2 | 3/2008 | Tsai | 267/136 |
| 7,566,296 B2 | 7/2009 | Zimmerling et al. | 600/25 |
| 7,608,035 B2 | 10/2009 | Farone | 600/9 |
| 7,642,887 B2 | 1/2010 | Zimmerling | 335/296 |
| 2004/0012470 A1 | 1/2004 | Zimmerling et al. | 335/207 |
| 2005/0001703 A1 | 1/2005 | Zimmerling | 335/220 |
| 2005/0062567 A1 | 3/2005 | Zimmerling et al. | 335/150 |
| 2006/0244560 A1 | 11/2006 | Zimmerling et al. | 335/207 |
| 2007/0053536 A1* | 3/2007 | Westerkull | 381/326 |
| 2007/0191673 A1 | 8/2007 | Ball et al. | 600/25 |
| 2007/0274551 A1 | 11/2007 | Tsai et al. | 381/326 |
| 2009/0209806 A1 | 8/2009 | Hakansson | 600/25 |
| 2010/0004716 A1 | 1/2010 | Zimmerling et al. | 607/57 |
| 2010/0145135 A1 | 6/2010 | Ball et al. | 600/25 |
| 2010/0324355 A1 | 12/2010 | Spitaels et al. | 600/25 |
| 2011/0022120 A1* | 1/2011 | Ball | A61N 1/08 607/57 |
| 2011/0216927 A1 | 9/2011 | Ball | 381/313 |
| 2012/0029267 A1 | 2/2012 | Ball | 600/25 |

FOREIGN PATENT DOCUMENTS

| | | | |
|---|---|---|---|
| JP | 04/023821 | 1/2004 | H04R 25/00 |
| SU | 1690749 | 11/1991 | A61F 11/04 |
| WO | WO 97/32629 | 9/1997 | A61N 1/32 |
| WO | WO 00/10361 | 2/2000 | |
| WO | WO 03/036560 A2 | 5/2003 | G06K 11/18 |
| WO | WO 03/081976 A2 | 10/2003 | |
| WO | WO 03/092326 A1 | 11/2003 | H04R 25/00 |
| WO | WO 2004/114723 | 12/2004 | H04R 25/00 |
| WO | WO 2011/011409 | 1/2011 | A61N 1/36 |
| WO | WO 2011/133747 | 10/2011 | A61N 1/36 |

OTHER PUBLICATIONS

Bromberg & Sunstein LLP, Response B filed Jun. 17, 2008 to Office Action dated Mar. 17, 2008, pertaining to U.S. Appl. No. 11/158,322, 10 pages.

Bromberg & Sunstein LLP, Response C filed Sep. 19, 2008 to Office Action dated Jun. 26, 2008, pertaining to U.S. Appl. No. 11/671,132, 8 pages.

Bromberg & Sunstein LLP, Response D filed Jan. 5, 2009 to Office Action dated Oct. 27, 2008, pertaining to U.S. Appl. No. 11/671,132, 13 pages.

European Patent Office, European Search Report (Extended) pertaining to Application No. 08075886.5-2205/12031896, date of mailing Jun. 3, 2009, 8 pages.

Heller et al, "Evaluation of MRI Compatibility of the Modified Nucleus Multichannel Auditory Brainstem and Cochlear Implants", *The American J. of Otology* 17(5); pp. 724-729 (Sep. 1996).

Hobbs, et al, "Magnetic Resonance Image—Guided Proteomics of Human Glioblastoma Multiforme", *Journal of Magnetic Resonance Imaging*; pp. 530-536 (2003).

International Searching Authority, International Search Report International Application No. PCT/IB03/02283, date of mailing Nov. 28, 2003, 7 pages.

International Searching Authority, Invitation to Pay Additional Fees—International Application No. PCT/IB2004/002588, date of mailing Dec. 20, 2004, 4 pages.

Teissl et al, "Cochlear Implants: In Vitro Investigation of Electromagnetic Interference at MR Imaging—Compatibility and Safety Aspects", *Radiology* 208(3); pp. 700-708 (Sep. 1998).

Teissl et al, "Magnetic Resonance Imaging and Cochlear Implants: Compatibility and Safety Aspects", *J. Magn. Reson. Imaging* 9(1); pp. 26-38 (Jan. 1999).

United States Patent and Trademark Office, Office Action dated Feb. 12, 2007, pertaining to U.S. Appl. No. 11/158,322, 6 pages.

United States Patent and Trademark Office, Office Action dated Mar. 17, 2008, pertaining to U.S. Appl. No. 11/158,322, 14 pages.

United States Patent and Trademark Office, Office Action dated Oct. 27, 2008, pertaining to U.S. Appl. No. 11/671,132, 7 pages.

International Searching Authority, Authorized Officer Lee W. Young, International Search Report and Written Opinion, PCT/US11/41045, mailed Oct. 25, 2011, 10 pages.

International Searching Authority, Authorized Officer Shane Thomas, International Search Report and Written Opinion, PCT/US12/70823, date of mailing Mar. 13, 2013, 13 pages.

International Searching Authority, Authorized Office Shane Thomas, International Search Report and Written Opinion, PCT/US13/28183, date of mailing May 10, 2013, 13 pages.

International Searching Authority, Authorized Officer Frank Liebmann, International Search Report and Written Opinion, PCT/US2013/049642, date of mailing Jan. 8, 2014, 11 pages.

\* cited by examiner

ELECTROMAGNETIC BONE CONDUCTION HEARING DEVICE

This application claims priority from U.S. Provisional Patent 61/669,161, filed Jul. 9, 2012, which is incorporated herein by reference.

FIELD OF THE INVENTION

The present invention relates to medical implants, and more specifically to a novel bone conduction hearing implant system.

BACKGROUND ART

A normal ear transmits sounds as shown in FIG. 1 through the outer ear 101 to the tympanic membrane 102 which moves the ossicles of the middle ear 103 that vibrate the oval window 106 and round window 107 membranes of the cochlea 104. The cochlea 104 is a long narrow duct wound spirally about its axis for approximately two and a half turns. The cochlea 104 forms an upright spiraling cone with a center called the modiolar where the spiral ganglion cells of the cochlear nerve 105 reside. In response to received sounds transmitted by the middle ear 103, the fluid-filled cochlea 104 functions as a transducer to generate electric pulses which are transmitted by the cochlear nerve 105 to the brain.

Hearing is impaired when there are problems in the ability to transduce external sounds into meaningful action potentials along the neural substrate of the cochlea. To improve impaired hearing, auditory prostheses have been developed. For example, when the impairment is related to operation of the middle ear, a conventional hearing aid or a middle ear implant may be used to provide acoustic-mechanical stimulation to the auditory system in the form of amplified sound. Or when the impairment is associated with the cochlea, a cochlear implant with an implanted stimulation electrode can electrically stimulate auditory nerve tissue with small currents delivered by multiple electrode contacts distributed along the electrode.

Middle ear implants employ electromagnetic transducers that convert sounds into mechanical vibration of the middle ear 103. A coil winding is held stationary by attachment to a non-vibrating structure within the middle ear 103 and microphone signal current is delivered to the coil winding to generate an electromagnetic field. A magnet is attached to an ossicle within the middle ear 103 so that the magnetic field of the magnet interacts with the magnetic field of the coil. The magnet vibrates in response to the interaction of the magnetic fields, causing vibration of the bones of the middle ear 103. See U.S. Pat. No. 6,190,305, which is incorporated herein by reference.

U.S. Patent Publication 20070191673 (incorporated herein by reference) describes another type of implantable hearing prosthesis system which uses bone conduction to deliver an audio signal to the cochlea for sound perception in persons with conductive or mixed conductive/sensorineural hearing loss. An implanted floating mass transducer (FMT) is affixed to the temporal bone of the skull. In response to an externally generated electrical audio signal, the FMT couples a mechanical stimulation signal to the temporal bone for delivery by bone conduction to the cochlea for perception as a sound signal.

SUMMARY OF THE INVENTION

Embodiments of the present invention include (Original) An external component for a bone conduction hearing implant. An external housing is fixedly attached on the skin of a hearing implant patient over an implanted bone conduction hearing transducer. An electromagnetic drive coil arrangement is fixed within the external housing for conducting electrical current to develop electromagnetic drive signals. An attachment magnet arrangement is suspended within the external housing by a flexible spring arrangement and magnetically coupled to the drive coil arrangement and to a corresponding implant magnet arrangement within the implanted bone conduction transducer. The electromagnetic drive signals magnetically interact with the attachment magnet arrangement which reacts by vibrating on the spring arrangement and magnetically interacting with the implant magnet arrangement to generate a bone conduction vibration signal by the implanted bone conduction hearing transducer for perception by the patient as sound.

There also may be a signal processor for generating electrical drive signals for the electromagnetic drive coils. The signal processor may be enclosed within the external housing, or within a signal processor housing separate from and connected to the external housing. There also may be at least one sensing microphone for developing an audio input signal to the signal processor.

The attachment magnet arrangement may be based on a cylindrical magnet suspended within and surrounded by the drive coil arrangement. Or the attachment magnet arrangement may be suspended within the external housing below the drive coil arrangement. The attachment magnet arrangement may include a first magnet having a first magnetic field orientation and a second magnet having a second magnetic field orientation opposite to the first magnetic field orientation. For example, the first magnet may be an inner cylinder magnet and the second magnet may be an outer ring magnet.

Embodiments of the present invention also include a hearing implant system having an external component according to any of the foregoing.

DETAILED DESCRIPTION OF SPECIFIC EMBODIMENTS

Conventional bone conduction implant arrangements may not optimally exploit the relatively large masses of the magnets that are used. Embodiments of the present invention are directed to an external component for a bone conduction hearing implant that better harnesses the inertial masses involved.

Figure 1:
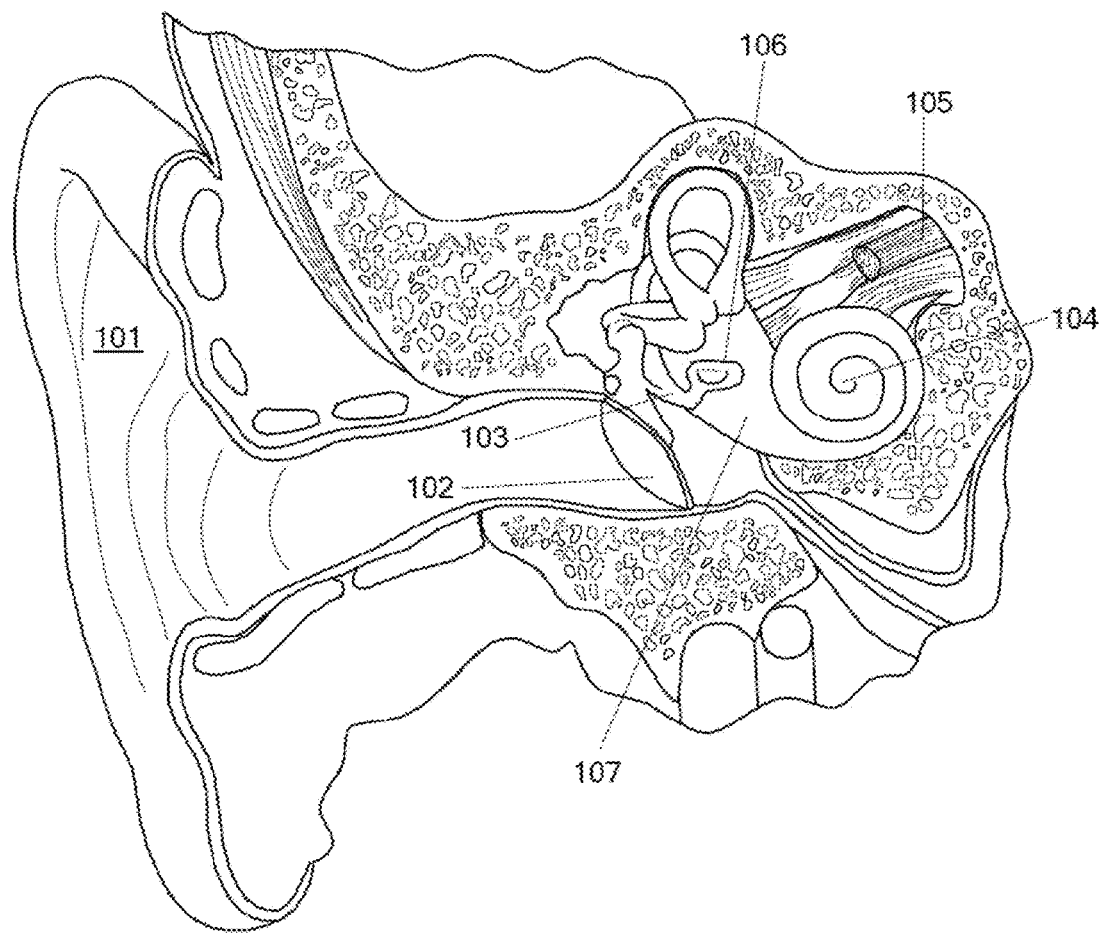
FIG. 1 shows anatomical structures of a typical human ear.
Figure 2:
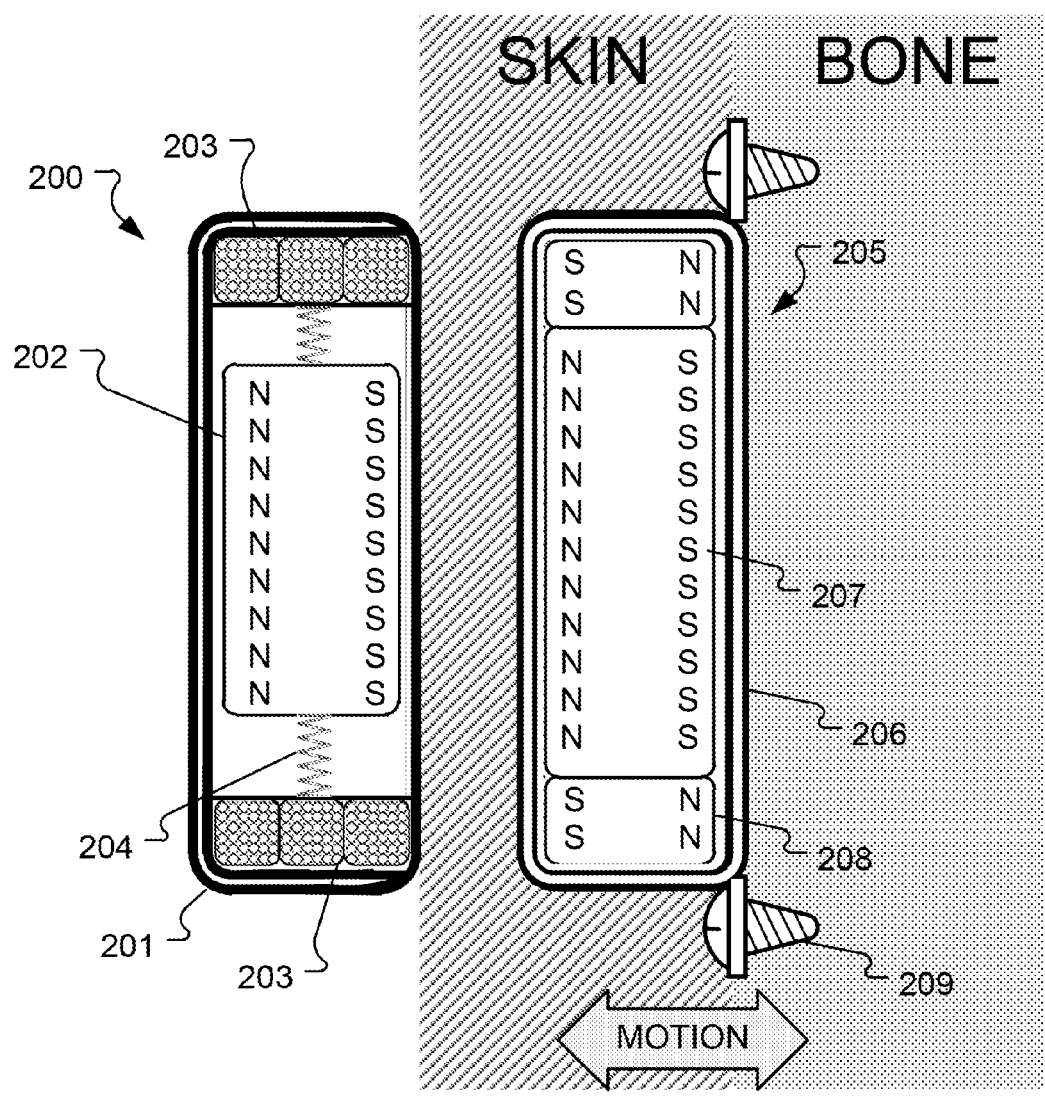
FIG. 2 shows various structural elements of an external component according to another embodiment of the present invention.

FIG. 2 shows various structural elements of an external component 200 having an external housing 201 that is fixedly attached on the skin of a hearing implant patient over an implanted bone conduction hearing transducer 205. The implanted transducer 205 is fixedly attached to the skull bone of the patient by bone attachment screws 209. An electromagnetic drive coil arrangement 203 is fixed within the external housing 201 for conducting electrical current to develop electromagnetic drive signals (generated by an external signal processor, not shown) for the implanted hearing transducer 205. A cylindrical attachment magnet 202 is suspended with the external housing 201 by a flexible spring arrangement 204. The cylindrical attachment magnet 202 also is surrounded by and magnetically coupled to the drive coil arrangement 203 and magnetically coupled to a corresponding center implant magnet 207 within the implanted bone conduction transducer 205. An outer ring magnet 208 surrounds the inner center implant magnet 207 and has an opposite magnetic field polarity which minimizes the net magnetic field of the implanted transducer 205.

The electromagnetic drive signals from the drive coil arrangement 203 magnetically interact with the attachment magnet arrangement 202 which reacts by vibrating on the spring arrangement 204 and magnetically interacting with the center implant magnet 207 to generate a bone conduction vibration signal by the implanted transducer 205 for perception by the patient through the skull bone as sound. The magnetic fields of the attachment magnet arrangement 202 and the outer ring magnet 208 do not interact significantly.

The signal processor that develops the electromagnetic drive signals from for drive coil arrangement 203 may be enclosed within the external housing 201, or it may be contained within a separate signal processor housing and electrically connected to the external housing 201. There also may be at least one sensing microphone for developing an audio input signal to the signal processor 210.

Figure 3:
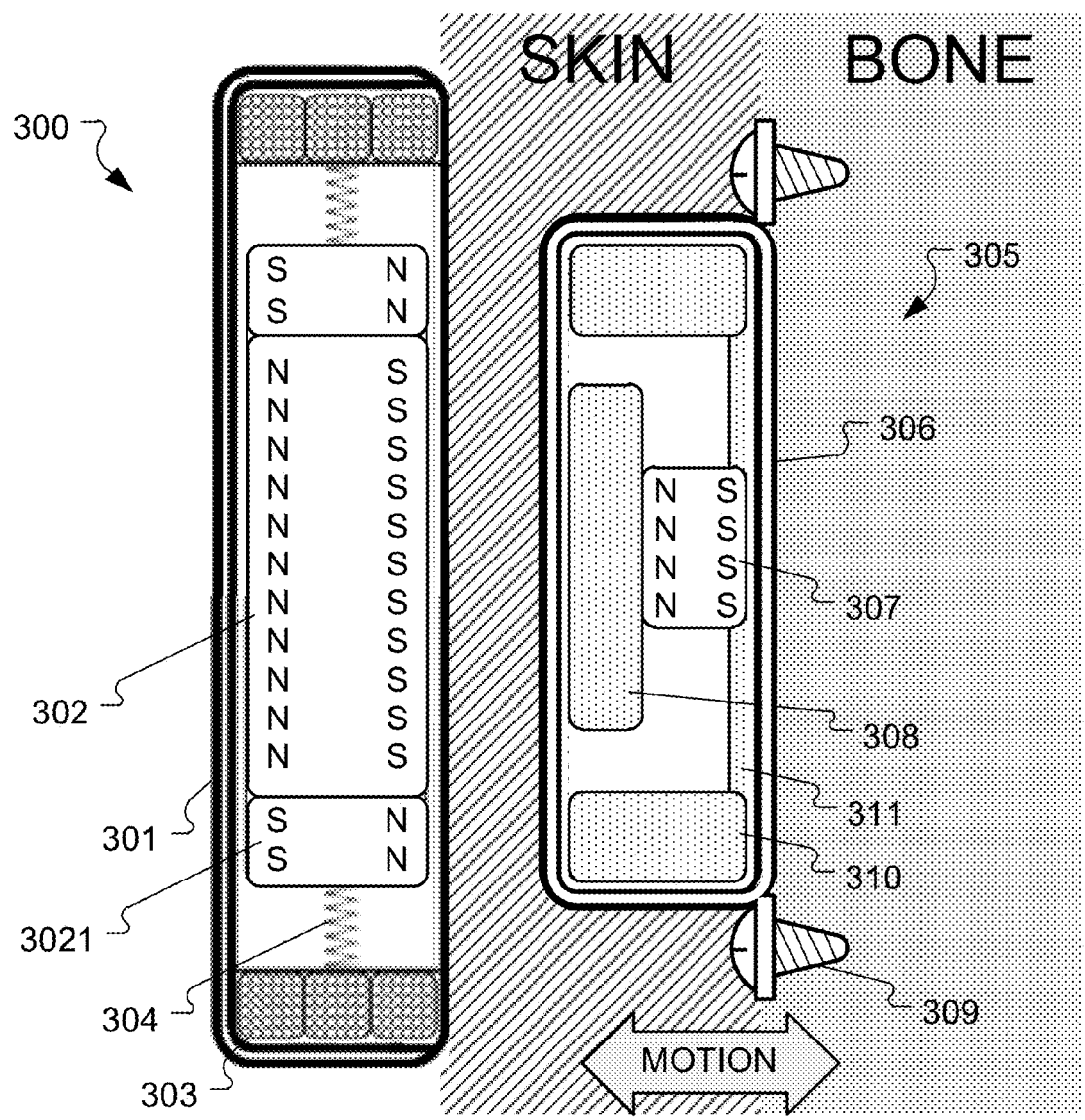
FIG. 3 shows various structural elements of an external component according to another embodiment.

FIG. 3 shows various structural elements of an external component 300 according to another embodiment in which the attachment magnet arrangement includes a center cylindrical attachment magnet 302 and an outer ring attachment magnet 3021 surrounding the inner cylindrical attachment magnet 302. The magnetic field orientations of the center cylindrical attachment magnet 302 and an outer ring attachment magnet 3021 are opposite to each other. The implanted transducer 305 in FIG. 3 has a small center implant magnet 307 and an arrangement of magnetic pole pieces including an outer pole piece 308 positioned atop the implant magnet 307, and outer pole pieces 310 radially around the implant magnet 307.

The electromagnetic drive signals from the drive coil arrangement 303 magnetically interact with the attachment magnet arrangement of the center cylindrical attachment magnet 302 and the outer ring attachment magnet 3021 which vibrate on the spring arrangement 304 and magnetically interact with the implant magnet 307 and pole pieces including 308 and 310 to generate a bone conduction vibration signal by the implanted transducer 305 for perception by the patient through the skull bone as sound.

Figure 4:
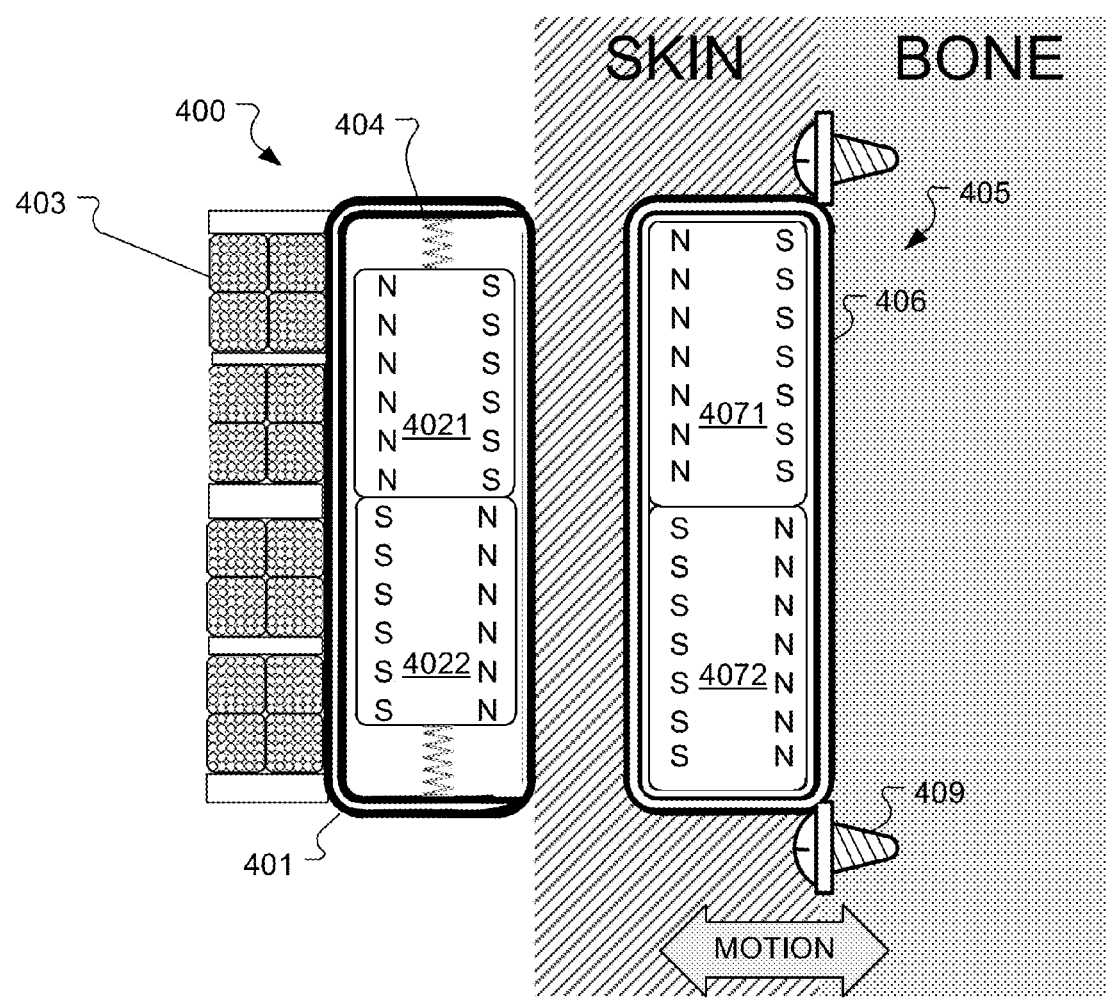
FIG. 4 shows various structural elements of an external component according to another embodiment.

FIG. 4 shows various structural elements of another embodiment of an external component 400 which has two magnetically opposite attachment magnets 4021 and 4022 which are suspended by a spring arrangement 404 within the external housing 401 below the drive coil arrangement 403. The implanted transducer 405 includes two corresponding implant magnets 4071 and 4072 which also are arranged to have magnetically opposite direction magnetic fields. Again, the opposite magnetic field polarities of the implant magnets 4071 and 4072 minimize the net magnetic field of the implanted transducer 405.

The electromagnetic drive signals from the drive coil arrangement 403 magnetically interact with the attachment magnet arrangement of the magnetically opposite attachment magnets 4021 and 4022 which vibrate on the spring arrangement 404 and magnetically interact with the implant magnets 4071 and 4072 to generate a bone conduction vibration signal by the implanted transducer 405 for perception by the patient through the skull bone as sound.

Figure 5:
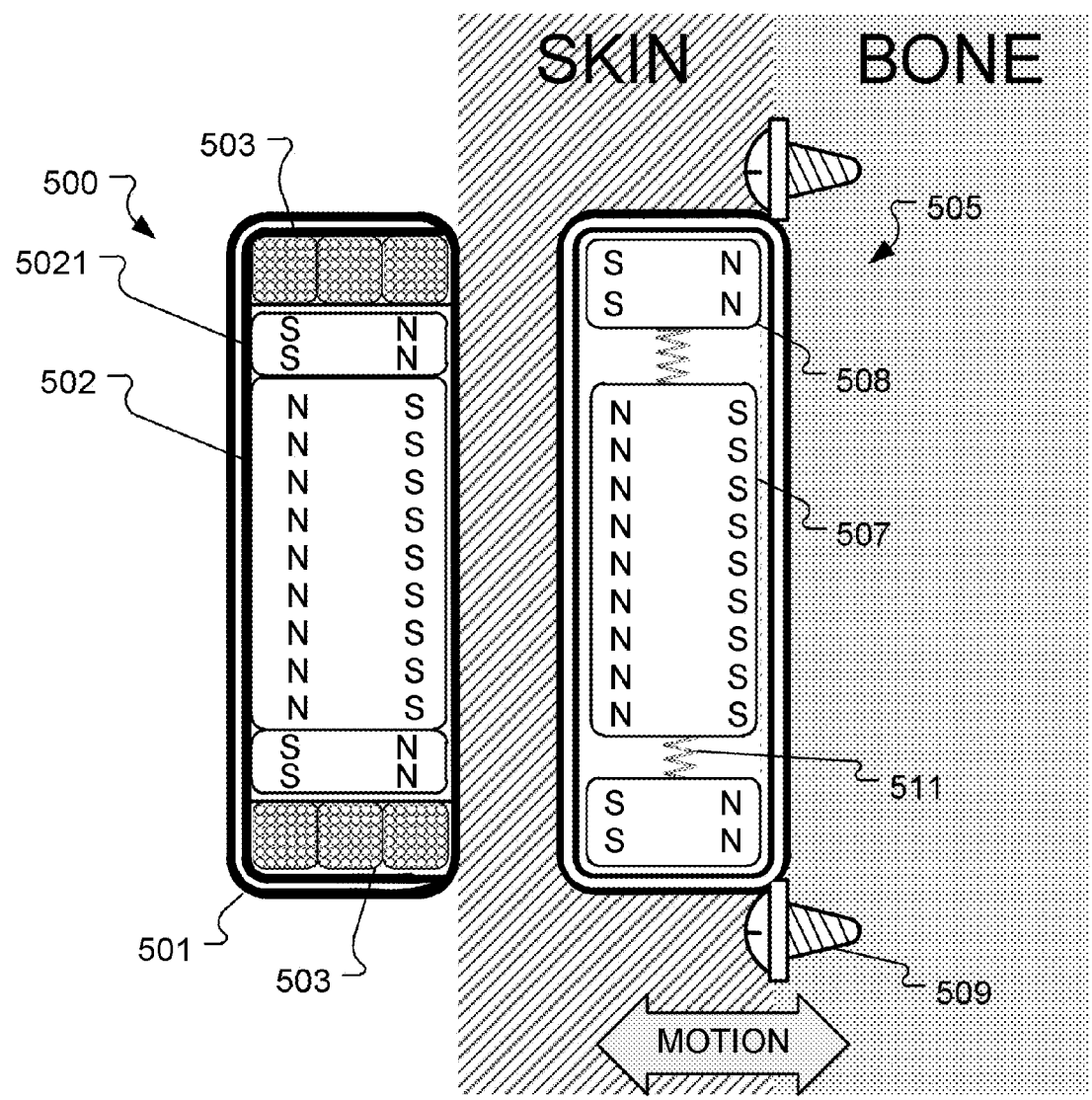
FIG. 5 shows various structural elements of an implantable bone conduction transducer according to another embodiment.

While the foregoing describe external components having attachment magnets suspended within the housing, the inertial mass of the implant magnets can also be exploited similarly suspending the implant magnets within the implant transducer housing. For example, FIG. 5 shows various structural elements of an implantable bone conduction transducer 505 according to one specific such embodiment. In this embodiment, a center implant magnet 507 is suspended within the implanted bone conduction transducer 505 by an implant spring arrangement 511 which is also connected to an outer ring implant magnet 508 that surrounds the inner center implant magnet 507 and has an opposite magnetic field polarity which minimizes the net magnetic field of the implanted transducer 505.

In the specific embodiment shown in FIG. 5, the external component 500 does not use a spring arrangement (though it could), but instead has an outer ring magnet 5021 that surrounds an inner center attachment magnet 502 with opposite magnetic field polarities that correspond to the magnetic field polarities of the implanted transducer 505 to optimize the magnetic field interaction. The electromagnetic drive signals from the drive coil arrangement 503 magnetically interact with the attachment magnet arrangement of the magnetically opposite outer ring magnet 5021 and inner center attachment magnet 502 which magnetically interact with the implant magnets 507 and 508 to generate a bone conduction vibration signal by the implanted transducer 505 for perception by the patient through the skull bone as sound.

Embodiments of the present invention such as those described above can be easily and directly implemented in existing products with corresponding size and geometry replacement magnets, either for the implanted magnet and/or the external magnet. Embodiments may usefully contain permanent magnetic material and/or ferro-magnetic material as well as other structural materials. These include without limitation magnetic ferrite materials such as $Fe_3O_4$, $BaFe_{12}O_{19}$ etc., compound materials such as plastic bonded permanent magnetic powder, and/or sintered material such as sintered NdFeB, SmCo, etc. Selection of the proper materials and arrangements may help avoid or reduce undesired eddy currents.

Although various exemplary embodiments of the invention have been disclosed, it should be apparent to those skilled in the art that various changes and modifications can be made which will achieve some of the advantages of the invention without departing from the true scope of the invention.

What is claimed is:

1. A bone conduction hearing implant system comprising:
    an implanted bone conduction hearing transducer with an implant magnet arrangement comprising an inner center magnet having a first magnetic field direction and an outer ring magnet surrounding the inner center magnet and having a second magnetic field direction opposite to the first magnetic field direction; and
    an external component comprising:
        i. an external housing for fixed attachment on the skin of a hearing implant patient over the implanted bone conduction hearing transducer;
        ii. an electromagnetic drive coil arrangement fixed within the external housing for conducting electrical current to develop electromagnetic drive signals; and
        iii. an attachment magnet arrangement suspended within the external housing and the electromagnetic drive coil arrangement by a flexible spring arrangement and magnetically coupled to the drive coil arrangement and to the implant magnet arrangement within the implanted bone conduction hearing transducer;

iv. wherein the electromagnetic drive signals magnetically interact with the attachment magnet arrangement to cause the attachment magnet arrangement to vibrate on the spring arrangement and magnetically interact with the inner center magnet without significantly interacting with the outer ring magnet of the implant magnet arrangement to generate a bone conduction vibration signal by the implanted bone conduction hearing transducer for perception by the patient as sound.

2. A bone conduction hearing implant system according to claim 1, further comprising:

at least one sensing microphone for developing an audio input signal to the external component.

3. A bone conduction hearing implant system according to claim 1, wherein the attachment magnet arrangement is a cylindrical magnet suspended within and surrounded by the drive coil arrangement.

4. A bone conduction hearing implant system according to claim 1, wherein the attachment magnet arrangement is suspended within and below the drive coil arrangement.

\* \* \* \* \*